(12) United States Patent
Gutman

(10) Patent No.: US 9,034,251 B1
(45) Date of Patent: May 19, 2015

(54) ADVANCED COMBINATION OZONE AND UV TREATMENT OF OBJECT OR PRODUCT IN-PACKAGE

(71) Applicant: Jose Gutman, Boca Raton, FL (US)

(72) Inventor: Jose Gutman, Boca Raton, FL (US)

(*) Notice: Subject to any disclaimer, the term of this patent is extended or adjusted under 35 U.S.C. 154(b) by 0 days.

(21) Appl. No.: 13/844,795

(22) Filed: Mar. 16, 2013

(51) Int. Cl.
*A61L 2/10* (2006.01)

(52) U.S. Cl.
CPC .................................... *A61L 2/10* (2013.01)

(58) Field of Classification Search
CPC .................................. A61L 2/10; A61L 2/202
USPC ............................................................ 422/24
See application file for complete search history.

(56) References Cited

U.S. PATENT DOCUMENTS

| | | |
|---|---|---|
| 6,403,033 B1 | 6/2002 | Gutman |
| 6,942,834 B2 | 9/2005 | Gutman |
| 7,976,777 B2 | 7/2011 | Gutman |
| 8,349,253 B2 | 1/2013 | Gutman |
| 8,754,385 B1 | 6/2014 | Gutman |

FOREIGN PATENT DOCUMENTS

RU 2110296 * 5/1998

* cited by examiner

*Primary Examiner* — Sean E Conley
(74) *Attorney, Agent, or Firm* — Jose Gutman; Fleit, Gibbons, Gutman, et al.

(57) ABSTRACT

A method for providing at least one of a sanitizing, disinfecting, and sterilizing treatment to a product or object while inside a package by treatment with a combination of UV energy and ozone to the product while in the package. The ozone can be provided inside the package through a gas channel secured, in a gas-tight seal, to an opening of the package containing the product or object. The ozone can also be generated in the package by converting oxygen to ozone in the package while containing the product or object therein.

20 Claims, 6 Drawing Sheets

ADVANCED COMBINATION OZONE AND UV TREATMENT OF OBJECT OR PRODUCT IN-PACKAGE

CROSS-REFERENCE TO RELATED APPLICATIONS

This application is a continuation-in-part of, and claims priority from, prior U.S. patent application Ser. No. 13/181,510, filed on Jul. 12, 2011, the entire disclosure of which is herein incorporated by reference, wherein such application is a continuation-in-part of, and claims priority from, prior U.S. patent application Ser. No. 11/226,123, filed on Sep. 13, 2005, now assigned U.S. Pat. No. 7,976,777, the entire disclosure of which is herein incorporated by reference, wherein such prior application was based upon, and claimed priority from, prior U.S. patent application Ser. No. 10/167,927, filed on Jun. 10, 2002, now assigned U.S. Pat. No. 6,942,834, the entire disclosure of which is also herein incorporated by reference, and wherein such prior application was based upon, and claimed priority from, prior U.S. patent application Ser. No. 09/583,041, filed on May 30, 2000, now assigned U.S. Pat. No. 6,403,033, the entire disclosure of which is also herein incorporated by reference, and wherein such prior application was based upon, and claimed priority from, prior U.S. Patent Application No. 60/136,885, filed on Jun. 1, 1999, the entire disclosure of which is also herein incorporated by reference.

FIELD OF THE DISCLOSURE

The present disclosure generally relates to treatment of products or objects with ozone and ultraviolet energy, and more particularly to a contained environment with ultraviolet energy sources for treating packaged products or objects inside their packages.

BACKGROUND

Objects or products such as perishable food products, including meats, poultry, fish, fruits, and vegetables, or objects such as medical devices and instruments, or other objects that may be subject to infection or contamination by micro-organisms or microbes, such as bacteria, viruses, and pathogens, typically require hygienic and sanitary conditions to be properly handled, packaged, and/or used. Food products, for example, can seriously degrade in shelf life and can be dangerous for consumption under unsanitary states. Medical devices and instruments are likewise subject to contamination from many sources and can cause serious harm if used in unsanitary conditions.

In the past, attempts to sanitize these types of objects have generally included washing and cleansing an object and then packaging and/or wrapping the object, which normally took place in special clean processing facilities. However, it is not always feasible or desirable to set up significant special facilities to sanitize such objects to desirable levels. For example, it may be desirable to package and/or wrap a food product at a convenient location where no special facilities are normally available such as at an office, a home, or even outdoors. Similarly, it may be desirable to package and/or wrap a medical device or instrument with no special medical cleansing facility being available or desirable for sanitizing the medical instrument before a subsequent use.

Regrettably, in most circumstances after providing sanitizing agents and cleansing facility to help clean and sanitize a product or object, subsequent poor handling by personnel typically results in re-contamination prior to final packaging of the product or object. This poor handling creates serious contamination hazards and transfer of disease to users and consumers of the products and objects being packaged under such conditions. Most commonly, an expensive special handling and processing facility is required to provide a sanitizing and/or sterilizing effect to an object or product. For example, irradiation processing of object and products requires very specialized and expensive equipment that is not readily usable in most environments.

With respect to perishable food products, such as meat, poultry, or fish, such products are normally packaged and re-packaged for subsequent use or distribution where at each stage of unpacking and re-packaging there is potential for introduction of contaminants, such as micro-organisms and viruses, and other pathogens, such as from *E-coli, salmonella*, and *listeria* contamination, that can harm humans as well as seriously degrade the shelf life, increase perishability, and detrimentally impact human consumability, of such food products. The normal handling conditions at the different stages of product distribution, ultimately to handling by an end user, and further the re-packaging at each one of the stages, causes additional risk for contamination of such food products.

Additionally, for providing sanitizing and/or sterilizing treatments to products and objects to be packaged and/or while packaged, it is desirable to expose the surfaces of the products and objects to the treatments. Surfaces of the multiple products and/or objects that remain unexposed to sanitizing and/or sterilizing treatments may likely continue to carry contaminants, including microbes such as bacteria and viruses that continue to pose contamination hazards to users and consumers of the products and/or objects. Therefore, sanitizing and/or sterilizing treatments that fail to treat the surfaces may not remove the necessary amount of contamination to result in desired sanitary and/or sterile conditions for the packaged products and/or objects. Unfortunately, a lack of treatment may not be detected after the products and/or objects are packaged. The contaminated products and/or objects after being packaged unfortunately may reach the user and/or consumer.

Food products, therefore, can include contaminants such as all sorts of micro-organisms, bacteria, and viruses. These contaminants can include, but are not limited to, bacteria, fungi, yeast, mold, mildew, and a variety of viruses. *E-coli, salmonella*, and *listeria* are pathogens that have gained much attention in the news where humans have been made sick and injured and have died as a result of contamination of food and water. Many of these types of contaminants can increase a rate of spoilage and reduce shelf life of food products as well as provide serious health hazards to humans that consume or come in contact with such products. Commonly, these contaminants are introduced to the surfaces of food products during processing, handling, and distribution.

Modern methods of packaging and cleaning food products, typically employed at food processing plants and factories, can reduce hazardous contaminants, such as micro-organisms, that can contaminate the surfaces of food products. These processing and packaging techniques include thermal processing, washing food products with chlorinated water, irradiation of food products, vacuum sealing packaging, low temperature storage, modified atmosphere packaging (or MAP), active packaging, and certain techniques for clean handling and packaging. Additionally, ozone bubbled in water has been used to wash and thereby disinfect chickens and other such food products and associated food processing plants and such specialized food handling environments.

Ozone in such aqueous solution has been generally regarded as safe for use with the food supply. For example, most people are familiar with ozonated drinking water. However, these processes and techniques discussed above typically must be applied under strictly controlled environments in a processing plant and factory and usually employing special equipment and handling.

These specialized requirements for packaging such food products, although helpful in reducing contamination and enhancing shelf life of products, are generally expensive and only available in special environments such as in food processing plants and factories. Further, when the packaging is removed at a later point in a distribution channel and the food product is re-packaged for further distribution or for consumption at a later time, new contamination can typically be introduced to the food products thereby losing some if not most of the beneficial effects of the earlier clean handling and packaging at the factory. This subsequent re-packaging and handling normally does not benefit from special equipment and ultra-clean environment to re-package the food products with heightened sanitary conditions as in a food processing plant and factory.

In medical applications, where medical equipment and instruments need to be sanitized, unfortunately, conventional specialized equipment must be used to sanitize and disinfect the equipment or instruments to a satisfactory level, or possibly sterilize as necessary, for further use. This specialized equipment is usually expensive and the process for sanitizing, disinfecting, and/or sterilizing, tends to be time consuming significantly impacting the costs of medical services and the commercial viability of medical businesses. Additionally, this specialized equipment and processing is normally not generally available in all but specialized environments.

Accordingly, there is a need for a system and method to eliminate the disadvantages of the prior art as discussed above, and particularly to provide a sanitizing, disinfecting, and/or sterilizing, application to objects and/or products being packaged.

BRIEF DESCRIPTION OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which.

DETAILED DESCRIPTION

Figure 1:
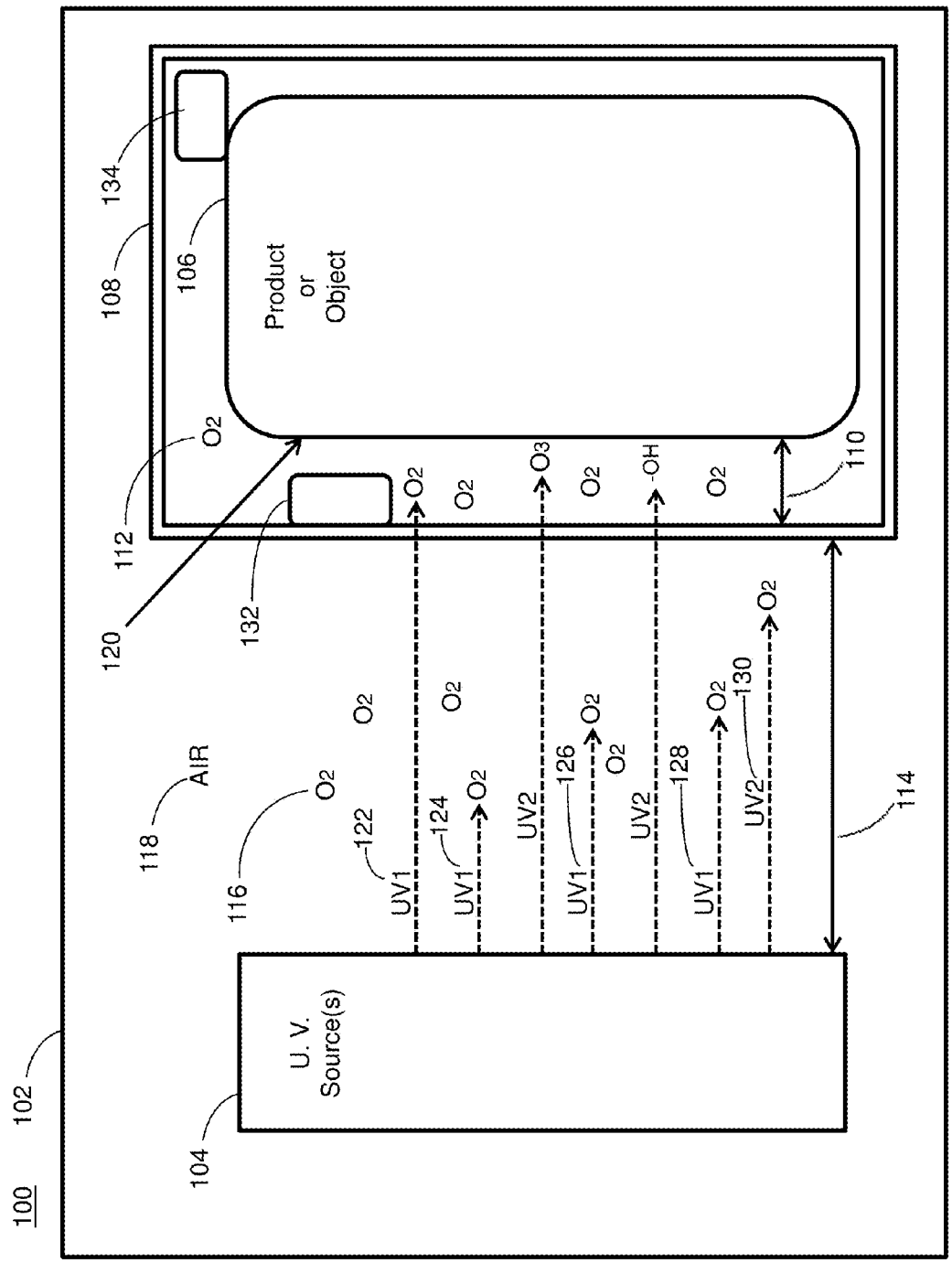
FIG. 1 is a side cut-away view of a first example of a sanitizing, disinfecting, and sterilizing system.

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the disclosed subject matter in virtually any appropriately detailed structure and function. Further, the terms and phrases used herein are not intended to be limiting, but rather, to provide an understandable description.

The terms "a" or "an", as used herein, are defined as one or more than one. The term plurality, as used herein, is defined as two or more than two. The term another, as used herein, is defined as at least a second or more. The terms "including" and "having" as used herein, are defined as comprising (i.e. open language). The term "coupled" as used herein, is defined as "connected" although not necessarily directly, and not necessarily mechanically.

The term "wireless communication device" is intended to broadly cover many different types of devices that can wirelessly receive signals, and in most cases can wirelessly transmit signals, and may also operate in a wireless communication system. For example, and not for limitation, an RFID device can communicate with a remote controller via wireless communication. It can identify itself and provide data, or optionally receive data, to-from the remote controller via wireless communication.

The terms program, software application, and the like as used herein, are defined as a sequence of instructions designed for execution on a computer system. A program, computer program, or software application typically includes a subroutine, a function, a procedure, an object method, an object implementation, an executable application, an applet, a servlet, a source code, an object code, a shared library/dynamic load library and/or other sequence of instructions designed for execution on a computer system.

While the specification concludes with claims defining the features of the invention that are regarded as novel, it is believed that the invention will be better understood from a consideration of the following description in conjunction with the drawing figures, in which like reference numerals are carried forward.

The present disclosure, according various embodiments, overcomes problems with the prior art by providing a contained environment where an atmosphere may be controlled and therein containing packaged products or objects that can be treated in-package by a sanitizing, disinfecting, and sterilizing treatment while optionally monitoring the inside of the package container to determine the presence of at least one of a sanitizing agent comprising ozone and ultraviolet radiation energy thereby monitoring the exposure of a product and/or object in the package container to the at least one of the sanitizing agent comprising ozone and the ultraviolet radiation energy. The exposure of the object or product to a sanitizing agent comprising ozone gas and/or to ultraviolet radiation energy in a storage volume in the package container effectively provides sanitizing, disinfecting, and sterilizing, treatment to the object or product captured or stored in at least one storage volume of the package container. However, by affirmatively monitoring this exposure inside the package container and by controlling the atmosphere in the contained environment it enhances the overall process to provide sanitizing, disinfecting, and sterilizing, treatment to the object or product.

Further, the term sanitizing agent comprising ozone gas is generally used herein to describe an agent that when transferred to a surface of an object or product at least provides the beneficial sanitizing, disinfecting, and sterilizing effects provided by ozone gas. Ozone gas has been shown very effective to sanitize, disinfect and sterilize equipment and processing facilities, as well as for ozonating drinking water. Ozone, in varying concentrations as a treatment for products and objects, can provide beneficial sanitizing, disinfecting, and sterilizing, effects thereto. Shortly after treatment, the ozone normally converts to a harmless composition usually resulting in oxygen associated with a treated product or object. For example, ozonated water additionally benefits from enhanced taste for human consumption.

The sanitizing agent comprising ozone gas, according to an embodiment of the present invention, provides at least a reduction in microbial count as part of a sanitizing application. Further, in certain applications, such as for medical sanitizing or other product sanitizing, the sanitizing agent comprising ozone gas can provide anti-viral and anti-pathogen properties to attack contaminants comprising viruses and other pathogens. Therefore, as anticipated by the embodiments of the present invention, and in accordance with specific applications thereof, the sanitizing agent comprising ozone gas provides anti-microbial properties to reduce microbial counts, including but not limited to reduction in bacteria, fungi, yeast, mold, and mildew, counts. Further, the sanitizing agent comprising ozone gas, according to alternative preferred embodiments of the present invention used in certain applications, additionally provides anti-viral properties to attack certain viruses. As is well known, ozone can exhibit such beneficial anti-microbial properties and anti-viral properties for specific applications of the embodiments of the present invention. Accordingly, the term sanitizing agent is used herein to comprise properties that can sanitize and disinfect, i.e., reduce microbial and viral counts, and/or sterilize, i.e., substantially minimizing counts thereof, with respect to an object or product being sanitized by the sanitizing agent comprising ozone gas and in accordance with specific applications. The term contaminants as used herein, therefore, includes such microbial and viral contaminants, and generally other invading contaminants, that can create unsanitary conditions, spoilage, and/or damage to objects or products. Additionally, it should be clear that the sanitizing agent comprising ozone provides beneficial sanitizing, disinfecting, and sterilizing effect while in close proximity to a surface of an object or product.

Referring to FIG. 1 the sanitizing, disinfecting, and sterilizing system 100 is shown. The system 100 comprises a contained environment 102. This contained environment 102 contains an atmosphere which may be different than the ambient atmosphere surrounding the contained environment 102. As shown in FIG. 1, one or more ultraviolet sources 104 are provided within the system 100. These ultraviolet sources 104 may include any of the known ultraviolet source devices, as an example, and not for limitation, including UV lamps, UV light emitting diodes, plasma generators, and the like. The contained environment 102 includes one or more contained spaces that can contain one or more UV sources 104 and one or more packaged products or objects 106. The product or object 106 is packaged inside packaging material 108. The product or object 106 is packaged within the packaging material 108 such that at least a portion of the product or object is contained within the packaging material 108. A space 110 between the outer surface of the product or object and the inner surface of the packaging material 108 contains an atmosphere as shown in FIG. 1. This atmosphere within the space 110 between the product or object 106 and the packaging material 108 includes oxygen 112. The atmosphere within the space 110 maybe different than the atmosphere within the contained environment 102. For example, the atmosphere within the contained environment 102 may include air 118 which includes oxygen 116. At the same time, the atmosphere within the space 110 may contain a mixture of gases that includes oxygen 112. However, other types of gases and/or fluids may be also contained within the space 110. In the example shown in FIG. 1, the atmosphere within the space 110 between the packaging material 108 and the product or object 106 is air. The UV sources 104 are located within the contained environment 102 such that UV energy may be radiated from the UV sources 104 toward the packaged product or object 106. The one or more UV sources 104 radiate UV energy toward the packaging material 108 and then pass through the packaging material 108 and into the atmosphere contained in the space 110 between the packaging material 108 and the outer surface of the product or object 106. When UV energy, such as UV 122, is radiated from the one or more UV sources 104 toward the packaged product or object 106 some of the UV energy 122 passes through the packaging material 108 and into the atmosphere within the space 110 which contains oxygen 112. By energizing the oxygen within the space 110 with the UV energy at a frequency range that energizes the oxygen it can convert the oxygen in the space 110 to other elements or compounds such as ozone. Additionally, it may convert the oxygen in the space 110 in combination with other elements or compounds in the space 110, such as moisture, into hydroxyl radicals. The ozone and optionally the hydroxyl radicals created in the space 110 within the packing material 108 creates a strong sanitizing, disinfecting and sterilizing agent that comes in contact with the surface of the product or object 106. Microbial contamination 120 on the surface of the product or object 106 may be sanitized, disinfected and sterilized by using this process of radiating ultraviolet energy into the space 110 and thereby converting an agent containing oxygen 112 in the space 110 to a sanitizing, disinfecting, and sterilizing agent containing ozone. Optionally, it may also create a sanitizing, disinfecting, and sterilizing agent containing hydroxyl radicals. In this way, microbial contamination 120 on the surface of the product or object 106 can be sanitized, disinfect and sterilized. Ozone is a strong oxidizing agent that has a very short half-life. Once the ozone, and optionally the hydroxyl radicals, oxidize and destroy the microbes on the product or object 106, the ozone inherently converts back to oxygen 112. The product or object 106 is now sanitized, disinfected, and sterilized and protected within the packaging material 108 from external contamination hazards.

Ultraviolet energy 122 of a wave-length approximately less than 200 nanometers with sufficient energy within the space 110 will effectively convert oxygen 112 to a second agent comprising ozone, or optionally hydroxyl radicals, that then treat the surface 120 of the product or object and sanitize, disinfect, and sterilize the product or object 106. Preferably, the ultraviolet energy 122 has substantially higher energy about the 185 nanometer wave-length range. More preferably, the ultraviolet energy 122 includes substantially higher energy about the 185 nanometer wave-lengths and has substantially reduced energy about the ultraviolet energy wave-lengths between 240 nanometers to approximately 280 nanometers. This ultraviolet energy 122, 124, 126, 128, energizes the oxygen molecules in the atmosphere and causes them to convert the sanitizing agent comprising ozone in the atmosphere. As shown in FIG. 1, oxygen molecules in the atmosphere within the contained environment 102 are also affected as well as the oxygen molecules in the space 110 between the surface 120 of the product or object 106 and the surface of the packaging material 108. Due to the strong interaction with oxygen in the atmosphere in the contained environment 102, the amount of the ultraviolet energy that actually reaches the packaging material 108 is significantly reduced. Further, the amount of the ultraviolet energy 122 that actually passes through the packaging material is further reduced. This leaves only a small amount of the ultraviolet energy 122 to interact and energize the oxygen within the space 110. This phenomenon must be considered in designing a system 100 such that sufficient amount of ultraviolet energy 122 reaches the atmosphere within the space 110. The distance 114 between the one or more ultraviolet sources 104 and the packaged product or object 106 is a significant factor in how much of the ultraviolet energy 122 will reach the space 110. Of course, the absolute level of ultraviolet energy 122 emitted from the one or more ultraviolet sources 104 can be increased to compensate for this loss of ultraviolet energy in the atmosphere between the ultraviolet sources 104 and the packaged product or object 106.

One way to affirmatively control the amount of ultraviolet energy 122 that reaches the atmosphere within the space 110 is by using one or more sensors 132, 134, within the space 110. These sensors 132, 134, may include ultraviolet energy sensing devices and/or ozone sensing devices. By monitoring the amount of ultraviolet energy 122 that reaches the sensors 132, 134 and/or monitoring the amount of ozone created within the space 110, the system 100 can provide feed-back to a controller that controls the amount of ultraviolet energy 122 being emitted from the UV sources 104. In certain applications, the sensors 132, 134, are strategically located within the space 110 between the product or object 106 and the inner surface of the packaging material 108 to monitor the UV energy and/or the ozone present within the space 110 in the vicinity of the one or more sensors 132, 134. In certain systems 100, the sensors 132, 134 may include RFID communication circuit such that a controller for the system 100 outside of the package 108 can communicate with each of the sensors 132, 134 and receive sensor data from each of the sensors 132, 134. The sensor data would indicate the detection of ultraviolet energy present in the space 110 in the vicinity of the particular sensor 132, 134, and, or a detection of a level of ozone within the space 110 in the vicinity of the particular sensor 132, 134. In this way, a controller for the system 100 to control UV sources 104 to optimally emit ultraviolet energy 122 in the contained environment 102 such that it reaches with sufficient energy into the space 110 and can convert the oxygen to ozone. The teachings of the technology used in the sensors 132, 134, and in the RFID communication, has already been discussed in the parent U.S. patent application Ser. No. 11/226,123, the teachings of which are incorporated by reference herein, and therefore will not be repeated.

In certain systems 100, a second ultraviolet energy 130 can be emitted from the one or more ultraviolet sources 104 at certain times. This second ultraviolet energy energizes the ozone in the atmosphere and accelerates the rate at which ozone converts back to oxygen. This second ultraviolet energy preferably comprises ultraviolet energy wave-lengths in the range from about 240 nanometers up to about 280 nanometers. More preferably, this second ultraviolet energy comprises a substantially increased amount of ultraviolet energy about the range of wave-lengths from 253 nanometers up to 270 nanometers. Additionally, this second ultraviolet energy more preferably has substantially reduced amount of ultraviolet energy at the range of ultraviolet energy wave-lengths below about 200 nanometers. This second ultraviolet energy can be used both as a strong antimicrobial ultraviolet energy treatment of the product or object 106 as well as to assist in converting ozone to oxygen in the atmosphere within the space 110 and within the contained environment 102. By using the second ultraviolet energy within the contained environment 102 it reduces the amount of ozone in the atmosphere in the contained environment 102 and thereby reduces the risk of ozone to humans that may, at times, need to have access to the contained environment 102. Additionally, this second ultraviolet energy reduces the amount of ozone within the package 108 again making it safer for humans to open the package 108 to access the product or object 106 in the package 108.

By treating the packaged product or object 106 within the contained environment 102 with the first ultraviolet energy 122, this converts the oxygen 112 in the space 110 to ozone and optionally to hydroxyl radicals thereby treating the product or object 106 to a sanitizing, disinfecting, and sterilizing treatment. Then, at an alternative time period, the ultraviolet sources 104 can be controlled to remove the first ultraviolet energy 122 and to emit the second ultraviolet energy into the contained environment 102 and into the packaging 108 and the space 110. In this way, by alternating between the first ultraviolet energy 122 and the second ultraviolet energy 130 the system 100 more effectively sanitizes, disinfects, and sterilizes the product or object 106 within the package 108 while at the same time it reduces the hazards to humans from excessively high levels of ozone possibly being present in the atmosphere within the contained environment and/or within the packaging 108.

Figure 2:
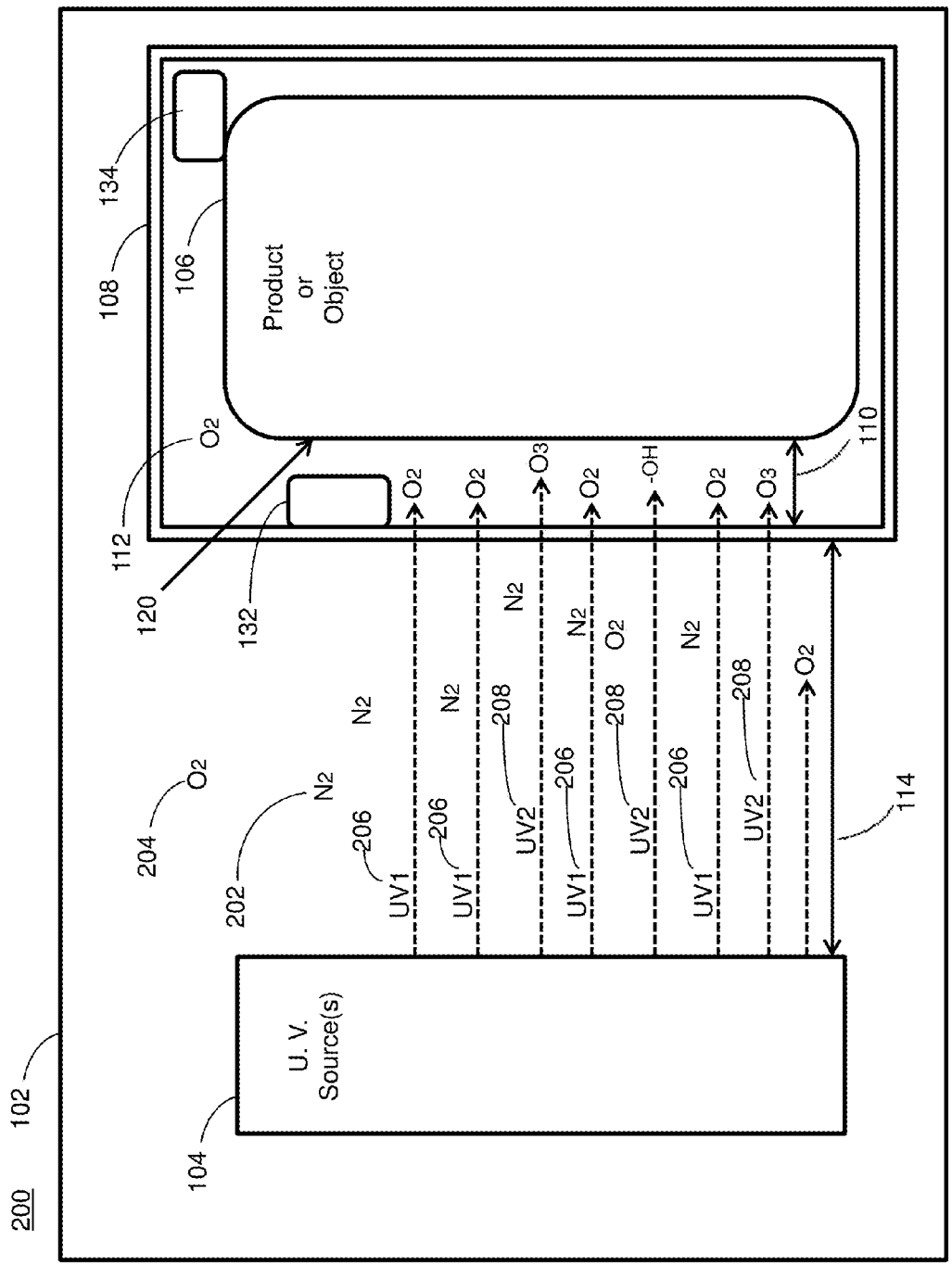
FIG. 2 is a side cut-away view of a second example of a sanitizing, disinfecting, and sterilizing system.

Referring to FIG. 2, a second sanitizing, disinfecting, and sterilizing system 200 is shown. It should be noted that figure ID element numbers that are the same to those shown in FIG. 1 indicate figure elements that are similar in this second system 200. The contained environment 102, as shown in FIG. 2, has an atmosphere that is substantially comprised of nitrogen 202. Small amounts of oxygen 204 may also be found in the atmosphere within the contained environment 102. However, preferably these amounts of oxygen 204 should be kept as low as possible, and most preferably to a trace amount. The large amount of nitrogen gas 202 in the atmosphere within the contained environment 102 has a beneficial effect on the ultraviolet energy that is emitted from the one or more ultraviolet sources 104. That is, there is very little to no oxygen 204 to energizeably interact with the ultraviolet energy 206, 208. Nitrogen 202 does not energizeably interact with the ultraviolet energy emitted from the one or more ultraviolet sources 104 at the desired wave-lengths, as has been discussed above. That is, the first ultraviolet energy 206 comprises ultraviolet energy wave-lengths below 200 nanometers, and most preferably with substantially higher amounts of ultraviolet energy at the wave-length range below 200 nanometers and about 185 nanometers, and with substantially reduced ultraviolet energy at the ultraviolet energy wave-lengths range between about 240 nanometers and 280 nanometers. The second ultraviolet energy 208 comprises ultraviolet energy wave-length at the range about 240 nanometers to 280 nanometers, and most preferably includes substantially increased amount of energy in the ultraviolet energy wave-length range from about 253 nanometers to 270 nanometers, and with substantially reduced ultraviolet energy at the ultraviolet energy range wave-length below 200 nanometers. As can be seen in FIG. 2, a much greater amount of ultraviolet energy, whether the first ultraviolet energy 206 or the second ultraviolet energy 208, propagates through the atmosphere within the contained environment 102 and reaches the packaging material 108 and passes through the packaging material 108 and reaches the atmosphere within the space 110 between the outer surface 120 of the product or object 106 and the inner surface of the packaging material 108. For comparison, see FIG. 1. This enhanced amount of ultraviolet energy that reaches the packaging material 108 is mainly as a result of the change in the composition of the atmosphere within the contained environment 102. That is, the atmosphere within the contained environment 102 now has little or no oxygen 204 to interfere with the transmission of the ultraviolet energy from the UV sources 104 to the space 110 within the package 108. Additionally, the nitrogen gas 202 within the atmosphere in the contained environment 102 does not significantly interact with the ultraviolet energy at the desired frequencies, as discussed above. In this way the ultraviolet energy transmits from the ultraviolet sources 104 into the space 110 with small attenuation. The high nitrogen composition of the atmosphere within the contained environment 102 therefore provides a medium for the ultraviolet energy to pass through without losing much of its ultraviolet energy level. Of course, the distance 114 between the UV sources 104 and the packaging material 108 will generally have an effect on the amount of ultraviolet energy that reaches the space 110. However, greater distance may be used between the UV sources 104 and the packaging material 108 while maintaining approximately the same level of ultraviolet energy that reaches the space 110.

While nitrogen gas 202 has been discussed above with respect to the composition of the atmosphere within the contained environment 102 to enhance the operation of the system 200, other combinations of gas compositions can alternatively be utilized. For example, use of noble gases in the atmosphere within the contained environment 102 to reduce the amount oxygen 204 also anticipated in alternative applications. Argon gas, or helium, can be used in the atmosphere within the contained environment 102. Other inert gases may be used in combination within the atmosphere of the contained environment 102 in alternative applications. A main objective, however, will be to significantly reduce, or remove, oxygen 204 from the atmosphere within the contained environment 102.

Different applications may include different combinations of gases as composition of the atmosphere within the contained environment 102, while reducing the level of oxygen 204 to a minimal or trace amount. In this way, a significantly enhanced amount of ultraviolet energy, 206, 208, will be delivered from the one or more ultraviolet sources 104 into the space 110 within the package 108. This then enhances the treatment of the product or object 106 by a sanitizing, disinfecting, and sterilizing treatment from the agent comprising ozone in the atmosphere within the space 110 as well as the ultraviolet energy that reaches the surface 120 of the product or object 106. Both the ozone and the ultraviolet energy are agents that kill and destroy microbes at the surface 120 of the product or object 106.

Various example applications of the present invention will be discussed in more detail below. These examples will be described using nitrogen as the main gas in the atmosphere of the contained environment 102. However, it should be understood that alternative gas compositions for the atmosphere within the contained environment 102 can also be used for alternative applications of the alternative embodiments of the present invention.

Figure 3:
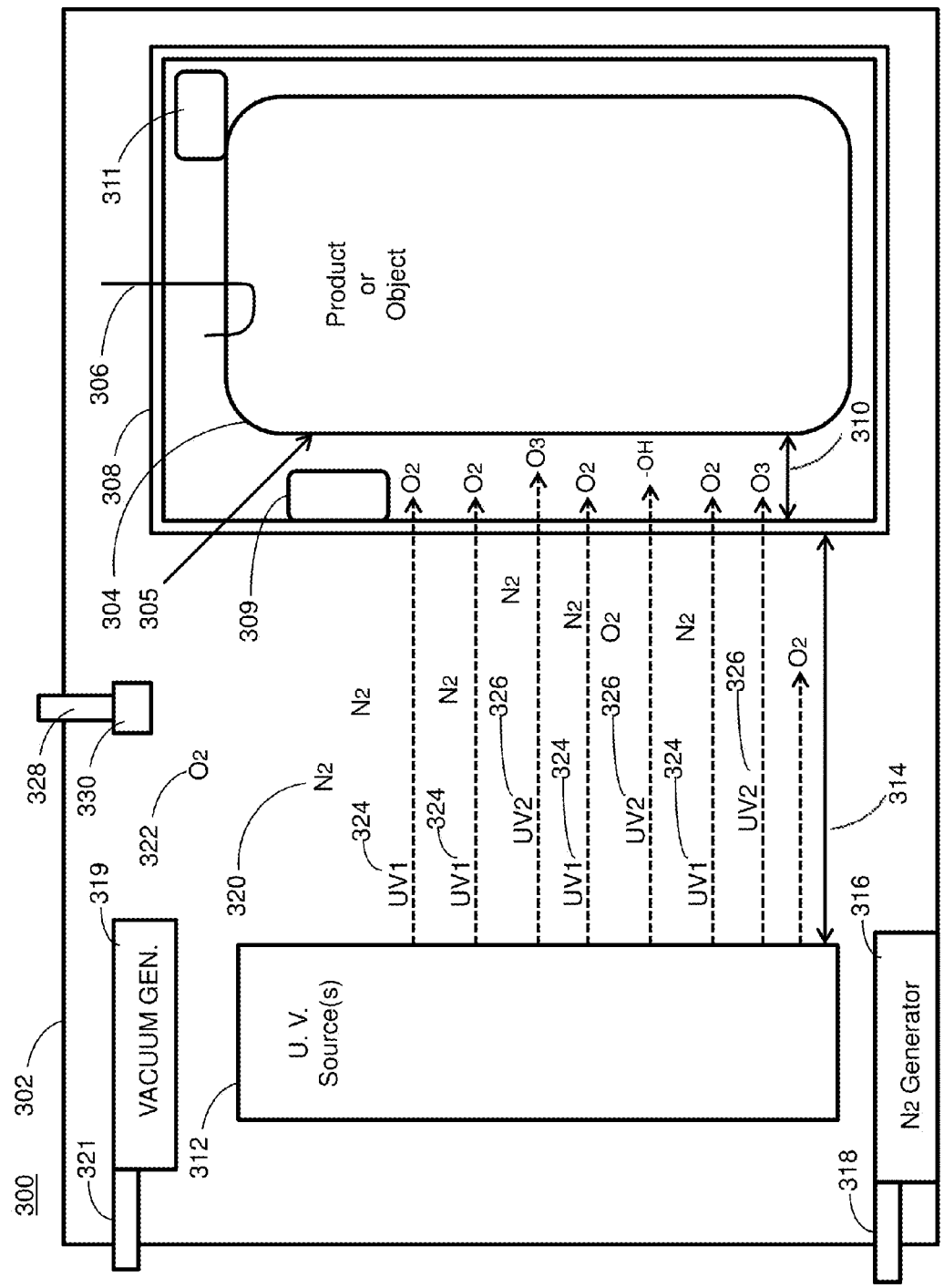
FIG. 3 is a side cut-away view of a third example of a sanitizing, disinfecting, and sterilizing system.

Referring to FIG. 3, an example embodiment is shown. A sanitizing, disinfecting, and sterilizing system 300 includes a contained environment 302. This contained environment, for example, may be a cargo hold in a carrier, a cargo transport in a train, a truck, a sea ship, an air ship, or another vehicle. In this contained environment 302 one or more packaged products or objects 304 are carried by hanging from supports 306, such as a hook 306, or other hanging support structure. For example, the product 304 can be an animal carcass or a fish, or other product that can be hanging from a hanging support 306 while being carried in a cargo transport 302.

The product or object 304 is, for example, wrapped in a plastic or polymeric sheet 308 which is the packaging material. The product may be for example an animal carcass. The animal carcass 304 hangs from a hook 306 inside of a train car, for example. This train car would be a refrigerated compartment holding one or more of these carcasses wrapped in the plastic sheet and hanging from hooks 306. A head space 310 between the inner surface of the packaging material 308, i.e. the wrapping sheet, and the outer surface 305 of the carcass 304 contains an atmosphere that comprises oxygen molecules. For example, air would be trapped within the space 310 when the carcass 304 is wrapped in the sheet 308.

The plastic sheet 308 is contrasted of one or more layers of polymer and/or plastic material that is generally transparent to the UV energy from the one or more UV sources 312 about UV energy wave-length ranges of interest, as has been discussed above. Optionally, sensors 309, 311, can be inserted into the space 310 when the carcass 304 is being wrapped in the sheet 308. These sensors 309, 311, sense any one or more of UV energy at the UV wave-length ranges of interest and sense a presence of ozone within the space 310 in the vicinity of the sensors 309, 311. The surfaces 305 of the carcasses 304 can be contaminated with microbes. According to the present example, therefore, one or more UV sources 312 are strategically located within the containment environment 302, i.e., the compartment in a refrigerated car and a train, in this example. The one or more UV sources 312 are located such that they emit UV energy through the atmosphere in the container environment 302 and that reach the packaging material 308 and pass through the packaging material 308 into the space 310. In this example, a first UV energy 324 is periodically transmitted from the UV sources 312 into the space 310 within the package 308. At other times, a second UV energy 326 is transmitted from the one or more UV sources 312 into the space 310. During operation of the one or more UV sources 312 the cargo compartment that is the container environment 302 is maintained closed and locked to prevent human access avoiding hazardous conditions for humans. The compartment 302 is closed and the atmosphere within the compartment 302 can be changed from generally an air atmosphere to an atmosphere that, in this example, contains mostly nitrogen 320. Although oxygen 322, in small or trace amounts, may be also found in the compartment 302. A controller (not shown) controls a vacuum generator 319 that flushes the gases from the compartment 302 through an exit port 321 outside of the compartment 302. For example, the air from the compartment 302 may be vacuumed by the vacuum generator 310 and ported by the port 321 to an ambient environment outside of the compartment 302. A nitrogen generator 316 is turned on by the controller to generate sufficient nitrogen 320 in the compartment 302. A port 318 coupled to the nitrogen generator 316 provides air to the nitrogen generator 316 to convert to the nitrogen gas 320 in the compartment 302. The controller may communicate with one or more sensors in the compartment 302 to monitor the atmosphere within the compartment reaching a desired concentration of nitrogen 320. These sensors and their communication with the controller are not shown. After the atmosphere in the compartment 302 reaches a sufficient concentration of nitrogen 320 the controller turns off the nitrogen generator 316 and the vacuum generator 319, thereby maintaining the contained environment 302 at a desired concentration of nitrogen in it's atmosphere. The one or more UV sources 312 then operate to periodically energize the first ultraviolet energy 324 and alternatively at other times energize the second ultraviolet energy 326. The first ultraviolet energy 324 converts oxygen in the space 310 to ozone. Optionally, hydroxyl radicals are also formed in the space 310. The second ultraviolet energy 326 energizes the ozone in the space 310 and accelerates it's conversion back to oxygen in the space 310. Additionally, the second ultraviolet energy 326 provides strong anti-microbial properties which additionally assist in killing and destroying microbes on the contaminated surface 305 of the carcass 304. The first ultraviolet energy 324 and the second ultraviolet energy 326, optionally, may be alternately pulsed to energize the oxygen in the space 310 thereby converting it to ozone followed by energizing the ozone to accelerate it's conversion back to oxygen in the space 310. This process can be repeated in cycles as desired by particular application to more effectively knock down and kill or destroy microbes on the surface 305 of the carcass 304. The sensors 309, 311, can be remotely monitored by the controller, such as using RFID technology that allows the controller to wirelessly monitor sensor data from the sensors 309, 311. Each sensor 309, 311, can be individually interrogated and it's sensor data can be downloaded to the controller. In this way, the controller can monitor the conditions within the space 310 inside the container 308 packaging the carcass 304. This sensor data feedback mechanism allows the controller to monitor and make sure that all carcasses hanging in the compartment 302 are being sufficiently treated to sanitize, disinfect, and sterilize the surface 305 of the carcass 304, according to requirements of particular applications.

Because the atmosphere in the compartment 302 is mostly nitrogen 320 the UV sources 312 are able to generate a lower amount of UV energy that substantially reaches the space 310 within the packaging material 308. This lower level of ultraviolet energy reaching the space 310 to sufficiently convert oxygen to ozone and then convert ozone back to oxygen provides certain advantages. For example, the ultraviolet sources 312 can be lower cost and can generate lower levels of ultraviolet energy thereby reducing the energy consumption of these ultraviolet sources 312 for particular applications. Additionally, the distance 314 between the ultraviolet sources 312 and the packaging material 308 of the individual hanging carcasses 304 can be extended while still providing sufficient ultraviolet energy within the space 310 inside the packaging material 308. This allows better coverage of hanging product within the compartment 302 with fewer ultraviolet sources 312. This results in easier more reliable configuration of ultraviolet sources 312 within the compartment 302, and lower cost of operation, which is important for commercial viability of a manufacturing and/or distribution facility or operation.

After the treatment of the packaged product 304 hanging by the hooks 306 in the compartment 302, human access to the compartment 302 can be made available after exhaust of the high concentration nitrogen atmosphere in the compartment 302 and flushed with fresh air into the compartment. That is, for example, the vacuum generator 319 is turned on by the controller to begin removing the atmosphere from within the compartment 302 while a controlled intake valve 330 and intake port 328 allow the controller to permit air from outside of the compartment 302 to be ported into the compartment 302. The combination of vacuum to remove the high nitrogen concentration atmosphere through an exit port 321 and allowing air to be flushed in through an input port 328 by a control valve 330 will restore a habitable environment within the compartment 302. Once a safe condition in the atmosphere within the compartment 302 has been reached and the one or more UV sources 312 are turned off, a lock on an access door to the compartment 302 may be released by the controller thereby allowing human access to the compartment 302.

Figure 4:
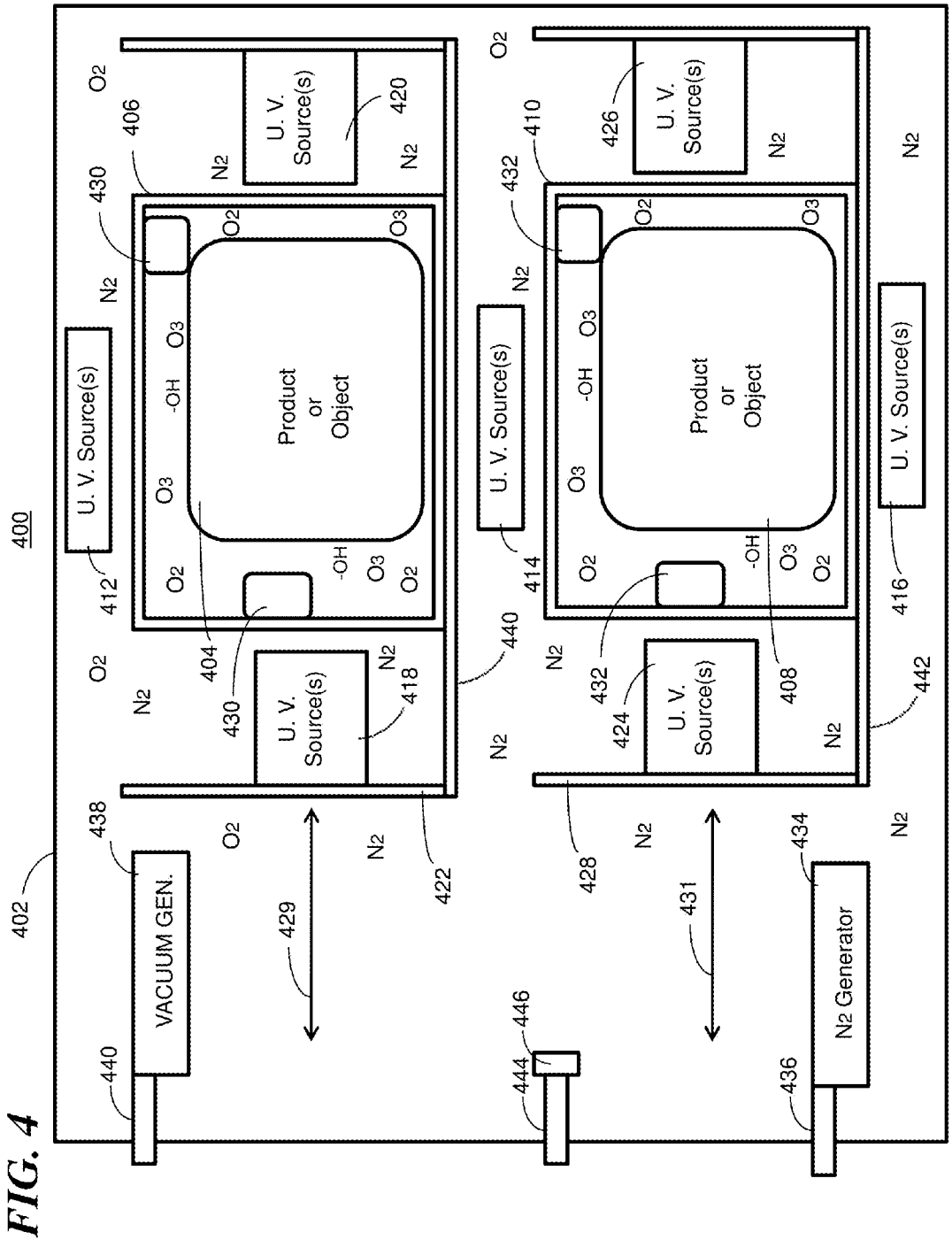
FIG. 4 is a side cut-away view of a fourth example of a sanitizing, disinfecting, and sterilizing system.

Referring to FIG. 4, another example application of embodiment of the present invention is shown. A sanitizing, disinfecting, and sterilizing system 400 comprises a contained environment 402. In this example, the contained environment 402 comprises one or more storage compartments within a storage locker, a refrigeration unit, a carrier and the like. One or more products or objects are individually packaged and stored in bins or compartments in shelves or drawers within the contained environment 402. For example, a refrigerator includes a separately contained section of the refrigerator with one or more drawers that can hold one or more products for providing sanitizing, disinfecting, and sterilizing treatment to the one or more products inside these drawers or shelves. As shown in FIG. 4, a first product or object 404 is at least partially contained by packaging material 406 creating a package 406 and closing at least a portion of the product or object 404. The first product or object 404 to be placed inside a space, such as a bin or compartment, inside of a moveable drawer 422 inside the storage region or section of the refrigerator. A drawer can move 429 as shown by the arrows such that the drawer can be pulled out and then product can be removed or product can be inserted into the drawer and then the drawer will be moved in the opposite direction to close the drawer and the contained environment 402 thereby creating a sealed section of the refrigerator which is the contained environment 402 for holding the product 404. A second product or object 408 can be packaged by packaging material 410 and located within a region, a space or bin of a second drawer 428 in the storage section 402 of the refrigerator. This second drawer 428 is moveable 431 as shown by the arrows. While the first drawer 422 and the second drawer 428 are shown as moveable structures it should be understood that these could also be permanent shelf type structures within a storage section of a refrigerator such that products or objects can be placed in these shelves and removed from the shelves. A plurality of ultraviolet sources are strategically located within the storage section 402 of the refrigerator such that the product 404, 408, can receive sanitizing, disinfecting, sterilizing treatment while located in the drawers 422, 428.

Certain UV sources 412, 414, 416, are located in the storage section 402 (contained environment) to provide ultraviolet energy to the products 404, 408, when stored in the storage section 402. These certain UV sources 412, 414, 416, are supported in the storage section 402 independent of any movement of the drawers 422, 428. Other UV sources 418, 420, 424, 426, are mounted in the drawers 422, 428, and move with the moving drawers 422, 428. The material composition of the drawers 422, 428, includes properties making the material substantially transparent to UV energy at the desired UV energy wave-length ranges as discussed above. For example, and not for limitation, the material composition of the drawers 422, 428, may include plastic, polymer, or quartz, or a combination thereof, that permits ultraviolet energy to substantially pass through the drawer material and thereby reach the packaging material 406, 410. The packaging material 406, 410, can include material that is also transparent or substantially transparent to ultraviolet energy, such as plastic film, certain plastic or polymer material, or even quartz material. The packaging material 406, 410, may form a rigid package 406, 410, or a semi-rigid or flexible package 406, 410. These different types of packages 406, 410, can all be supported in various applications of embodiments of the present invention. While not shown in FIG. 4, one or more energy sources are electrically coupled to the one or more ultraviolet sources 412, 414, 416, 418, 420, 424, 426, thereby providing electrical power to operate the UV sources under control from a controller (not shown). Sensors 430, 432, inside the packages 406, 410, respectively, can be monitored by the controller, such as the wireless communication using RFID communication, to monitor the levels of ultraviolet energy and/or ozone detected inside the packages 406, 410. Once the contained environment 402 is closed and locked, protected from human access, the controller can turn on the nitrogen generator 434 and the vacuum generator 438 to change the atmosphere within the contained environment 402 from a general air atmosphere to a mostly nitrogen atmosphere. The nitrogen generator 434 utilizes an input port 436 to draw in air which it then converts into mostly nitrogen which is provided to the contained environment 402. The vacuum generator 438 draws out the gas atmosphere from the contained environment 402 and ports it through a port 440 outside of the contained environment. One or more sensors within the contained environment 402 (not shown) are monitored by the controller to determine when the atmosphere within the contained environment 402 has reached a sufficient concentration of nitrogen to then proceed to operate the ultraviolet sources. Once the controller determines that the atmosphere has reached a sufficient concentration of nitrogen the controller then turns off the nitrogen generator 434 and turns off the vacuum generator 438. The contained environment 402, with the mostly nitrogen atmosphere, is now ready for operating the ultraviolet sources 412, 414, 416, 418, 420, 424, 426. A first ultraviolet energy is periodically emitted from the ultraviolet sources through the atmosphere of the contained environment 402 and to the packaging material 406, 410 of the packaged products 404, 408. The first ultraviolet energy passes through the packaging material 406, 410 and enters the space between the product or object 404, 408, and the inner surface of the packaging material 406, 410. Within this space inside the packages 406, 410, the atmosphere includes oxygen molecules. The ultraviolet energy sources periodically emit the first ultraviolet energy into the space within the packages 406, 410 such that it converts the oxygen molecules through ozone. Optionally, hydroxyl radicals are also created within the space inside the packages 406, 410. The combination of ozone, optional hydroxyl radicals, and ultraviolet energy inside the packages 406, 410, provide a sanitizing, disinfecting, and sterilizing treatment to the products or objects 404, 408. At alternate periods of time the ultraviolet sources stop emitting the first ultraviolet energy and emit a second ultraviolet energy that when it reaches inside the space within the packages 406, 410, it accelerates conversion of the ozone back to oxygen and provides an anti-microbial treatment to the surfaces of the products or objects 404, 408. The sensors 430, 432, are used by the controller to monitor the sensed conditions of ultraviolet energy levels and/or ozone levels within the spaces inside the packages 406, 410. In this way, the controller can monitor using the feedback from the sensors 430, 432, to more effectively maintain a desired treatment of the product or objects 404, 408 inside the packages 406, 410.

For example, the ultraviolet energy sources may periodically pulse the first ultraviolet energy into the space within the packages 406, 410, and then at other time periods would pulse the second ultraviolet energy into the spaces within the packages 406, 410. The times in between these pulses, in certain embodiments, could be extended with no ultraviolet energy being emitted into the contained environment 402. By exposing the products or objects 404, 408, to short time periods of the first ultraviolet energy and the second ultraviolet energy, sufficient to provide the treatment for sanitizing, disinfecting, and sterilizing the products or objects 404, 408, the system 400 maintains optimal treatment of the packaged product 404, 408. These treatment processes also reduce the amount of exposure to the ultraviolet energy by the products or objects 404, 408, to as necessary to maintain treatment of these products or objects 404, 408. However, by the products or objects 404, 408. Excessive exposure to these ultraviolet energies may affect attributes of certain products or objects 404, 410. So by reducing the exposures to these ultraviolet energies to only be required amounts to maintain a treatment periodically significantly enhances and maintains the desired attributes and qualities of these products or objects, 404, 408, that are packaged 406, 410, and stored in the contained environment 402. To permit access to the contained environment 402, after treatment, the ultraviolet sources are turned off by the controller, and the vacuum generator 438 is turned on to port via the port 440 the atmosphere from within the contained environment 402 to outside of the contained environment while a control valve 446 allows air to be ported into the contained environment via the input port 444. When the sensors within the contained environment 402 indicate to the controller that the atmosphere has reached habitable conditions, such as an air atmosphere, within the contained environment 402, the controller may turn off the vacuum generator 438 and release a lock to an access door into the contained environment 402. For example, the drawers 422, 428, may be locked and sealed in a contained environment 402 until the atmosphere within the contained environment 402 reaches substantially an air atmosphere. The controller then releases the drawers so that they can be pulled out 429, 431 by a human access.

While a nitrogen generator 434 has been described in the examples herein, for creating the mostly nitrogen atmosphere inside the contained environment 402, it should be understood that other gas control mechanisms may be used to create the nitrogen atmosphere in the contained environment 402. For example, a gas pump may replace the nitrogen generator 434 and the nitrogen may be contained in an external containment structure such as a tank or other holding space. When nitrogen is desired to be flushed into the contained environment 402 the controller may control a pump 434 that would draw nitrogen from a separate container outside of the contained environment 402 and provide the nitrogen gas into the atmosphere within the contained environment 402. In certain environments, the nitrogen generator 434 may be replaced with a gas pump 434 that can operate in two separate directions and thereby can flush nitrogen atmosphere into the contained environment 402 from an external containment structure when nitrogen atmosphere is desired to be flushed into the contained environment 402, or alternatively can draw out the atmosphere from the contained environment 402 and into the external containment structure.

Figure 5:
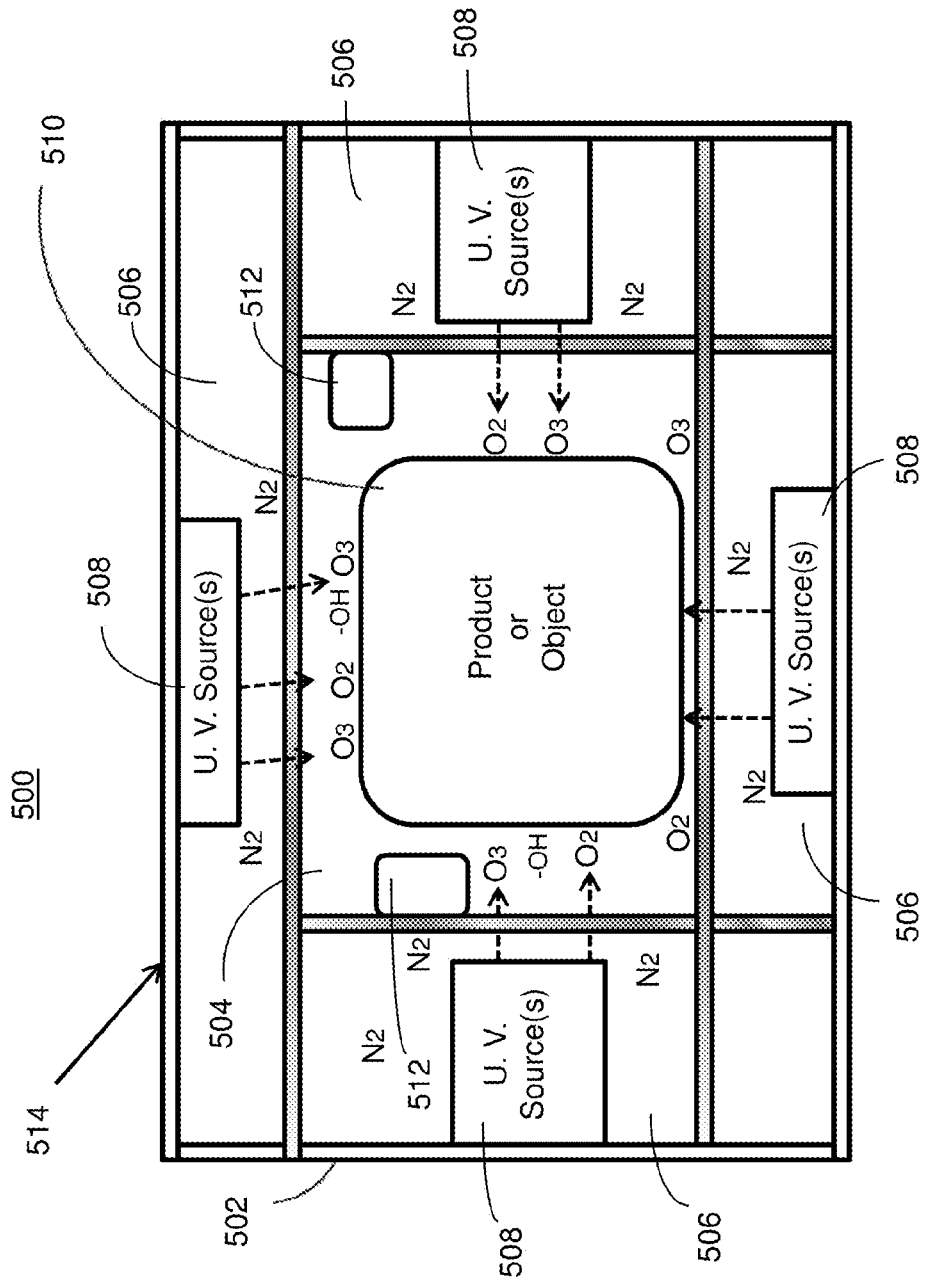
FIG. 5 is a side cut-away view of a fifth example of a sanitizing, disinfecting, and sterilizing system.

FIG. 5 illustrates a multi-compartment package 502 that holds a product or object 510 in a main compartment 504, and including packaging material dividing the compartments 506 from the main compartment 504 that comprises a composition that allows the ultraviolet energy from the ultraviolet energy sources 508 to pass through the packaging material and into the main compartment 504. This package 502 may be constructed of a rigid, semi rigid, or a flexible construction. For example, the package 502 that contains the product or object 510 can be constructed in the shape of a box, or a cylinder, or other type of container that holds a product or object 510 in a main compartment 504 inside the package 502. A top (or lid) 514 of the package 502 can be removed to permit access to the main compartment 504 to place a product or object 510 in the main compartment 504 or to remove the product or object 510 from the main compartment 504. UV sources 508 are located within separate chambers 506 from the main compartment 504. These separate chambers 506 are filled with nitrogen gas atmosphere, or substantially a nitrogen gas filled atmosphere, such that there is little to no oxygen molecules in these chambers 506. The UV sources 508 emit the first ultraviolet energy to convert oxygen to ozone within the main compartment 504 and alternatively emit the second ultraviolet energy to convert the ozone back to oxygen in the main compartment 504, as shown in FIG. 5. Optionally, hydroxyl radicals are also created in the main compartment 504. In this way, a sanitizing, disinfecting, and sterilizing treatment is provided to the product or object 510 in the main compartment 504. The UV sources 508 are powered by one or more energy sources (not shown). Sensors 512, within the main compartment 504, may include ultraviolet energy sensing devices and/or ozone sensing devices. By monitoring the amount of ultraviolet energy that reaches the sensors 512 and/or monitoring the amount of ozone created within the head space atmosphere in the main compartment 504, feedback can be provided to a controller (not shown) that controls the amount of ultraviolet energy being emitted from the UV sources 508. The package 502 containing the product or object 510 in the main compartment 504, is transportable and it provides the desired treatment to the product or object 510 while protecting the product or object 510 from external contamination hazards.

Figure 6:
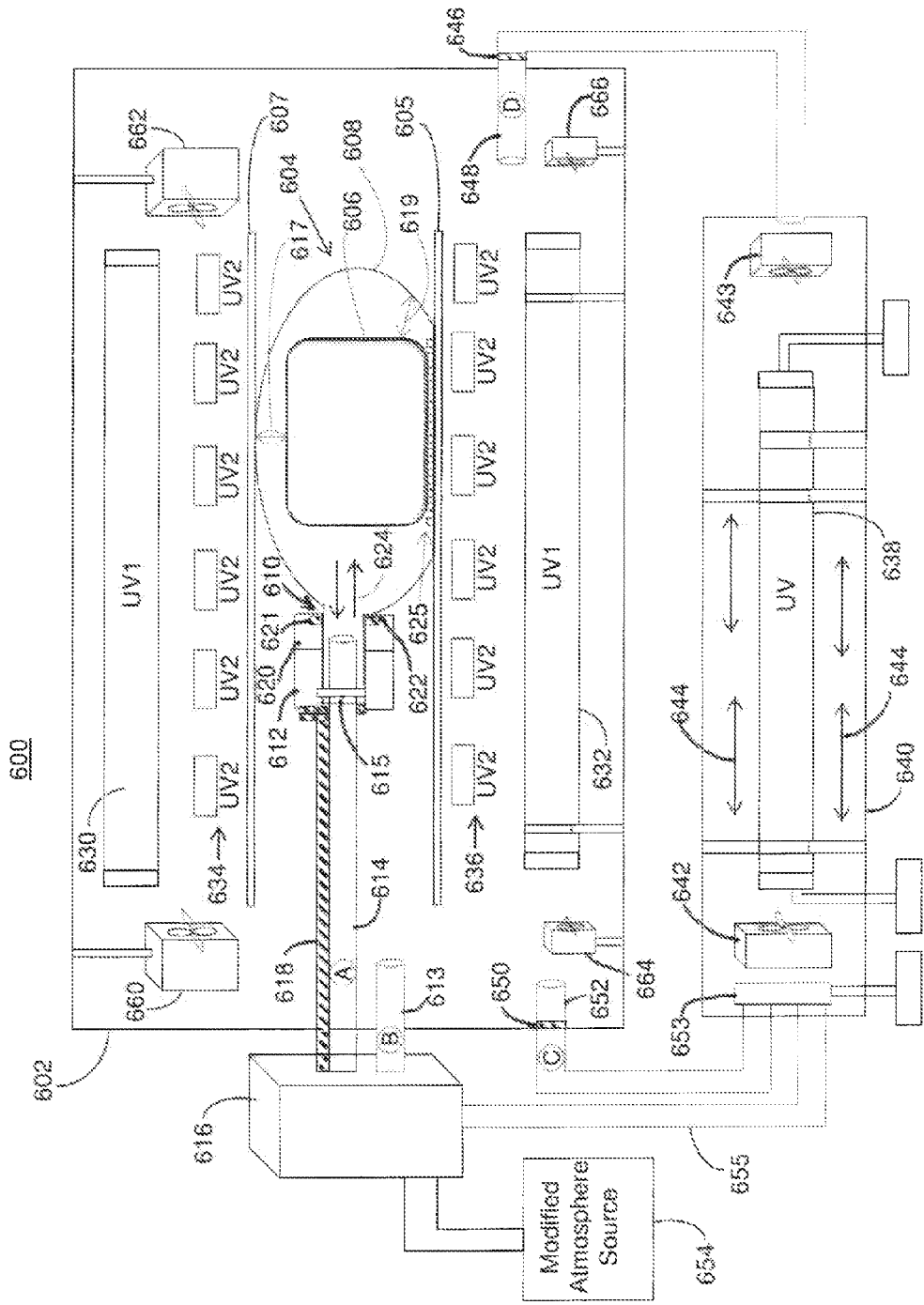
FIG. 6 is a side cut-away view of an advanced combination ozone and UV treatment system, according to one embodiment of the present disclosure.

With reference to FIG. 6, an advanced combination ozone and UV treatment system 600 is shown, according to one embodiment of the present disclosure. A chamber 602 provides an operating environment for this embodiment. Alternatively, instead of a chamber, a compartment, a storage container or other containing device may be used in alternative embodiments. The container 602 is accessible by a user to locate an object or product in its own package 604 in the operating environment of the container 602. The product or object 606 is stored in its own packaging 608. The packaging can take many different types of forms. In this example, the packaging comprises a film wrapping 608 around at least a portion of a product or object 606 contained therein. When the product or object 606 is in the packaging 608 typically there is a head space 617, 619, around the product 606 in the packaging 608. The head space will contain air when the product is initially placed in the package 608. However, as will be discussed in more detail below, the head space 617, 619, may contain other modified atmosphere gases or may be vacuum sealed to almost no gas being contained in the package 608.

With the user placing the product or object in its packaging 604 into the container or hamber 602, the mouth portion of the package 610 (or another opening in the package 608) is fitted over a nozzle 614 that provides a channel for moving gas into the package 608 and out of the package 608 as indicated by the two arrows 624. Toward an end portion of the nozzle 614 a holding fixture with a moveable top portion and bottom portion 612 can be moved over the mouth or opening 610 and clamped by the retaining structure 615. This creates an air tight seal at the end of the opening 610. The nozzle 614 extends into the inner portion of the package 608 and the clamp 615 holds securely the opening 610 of the package 608 to the nozzle 614. The nozzle is labeled A in this example. An electrical harness 618 provides electrical signals and power to circuits in the holding structure 612 as will be discussed in more detail below.

The nozzle labeled A is communicatively coupled with a bi-directional pumping system 616 as shown. The pump 616 can take many different forms. However, it can draw air out of the inner package 608 to create a vacuumed environment in the package 608, can pump or puff air or gas through the nozzle 614 and into the inner package 608 as indicated by the two arrows 624, or can be directed to alternative gas coupling paths, such as pipe labeled B 613, modified atmosphere source 614 coupled to the pump 616, pipe labeled C 652 which is connected through a valve system 653 to a gas coupling path 655 with the pump mechanism 616, and can be coupled to separate chamber 640 via the gas coupling path 655 as will be discussed below.

After the product in packaging 604 is placed into the container 602 it is clamped by the clamp structure 615 onto the nozzle labeled 614 and securely held there by the holding mechanism 612 as shown. According to the present example, the user can actuate the holder mechanism 612 and move it to secure around the package 608 at the nozzle 614. The mouth of the package 610 is held sealed to the nozzle 614 such that air or gas in the general environment inside the container 602 will not enter into the package 608. However, the pump 616 can control what gas (e.g. air, ozone, modified atmosphere gas such as nitrogen, carbon dioxide, or other gas from the modified atmosphere source 654). The product in package 604 can be placed by the user on a support such as a quartz glass base 605 that allows UV light to substantially pass through the quartz 605. Optionally, a second dividing quartz sheet 607 is located above the product in package 604. These sheets 605, 607, and other possible sheets on other sides surrounding the product in package 604 do not impede the transmission of UV energy from various UV sources that may be activated in the compartment or chamber 602. These various arrangements of one or more UV sources relative to the product in package 604 and the one or more divider structures such as made of quartz 605, 607, will be discussed below.

With the product in package 604 being secured at its mouth 610 to the nozzle 614, the pump 616 can turn on movement of gas into or out of the package 624 as shown. The source or destination of the moving gas into or out of the package 608 can vary depending on the application, as will be discussed below. A first set of UV sources 630, 632, can be activated in the operating environment in the chamber 602. This first set of UV sources 630, 632, operate at a UV frequency band that tends to generate ozone gas from the oxygen in the air in the operating environment of the compartment 602 as well as the oxygen in the atmosphere inside the package 608 as indicated by the head space 617, 619 double headed arrows. To generate ozone gas in the space 617, 619, the system 600 can energize the first set of UV sources 630, 632 in the environment in the chamber 602 and the UV energy from the first set of UV sources 630, 632 will pass through the package 608 and into the head space 617, 619, in the package 608. Oxygen in the head space 617, 619, will be converted to ozone. Oxygen in the environment inside the chamber 602 will also be converted to ozone. Where the atmosphere in the container 602 started with air, it will increase in ozone concentration with the first set of UV sources 630, 632, energized. The system 600 can monitor with sensors (not shown) in the environment in the container 602 this concentration of ozone in the ambient atmosphere in the container 602. As the ozone concentration increases in the ambient atmosphere surrounding the package 608 the pump 616 can be turned on by the system controller (not shown) to draw the concentration of ozone gas from the ambient atmosphere in the chamber 602 through the gas connection 613 and pass the ozone concentrated gas into the head space 617,619 in the package 608. A separate one or more ozone sensors can be located in the environment in the chamber 602 to monitor the ozone concentration in the ambient atmosphere in the container 602. By moving gas from the ambient atmosphere in the container 602 into the head space 617, 619, a desired ozone concentration may be attained more quickly by the system 600 than from only the UV energy from the first set of UV sources 630, 632, entering the head space 617, 619, in the package 608. However, this UV energy additionally provides a sanitizing, disinfecting, and sterilizing treatment to the surfaces of the product 606 in the package 608 that are exposed to the UV energy from the first set of UV sources 630, 632. This combination of ozone gas in the head space 617, 619, being puffed into the package 608 by the pump 616 through the nozzle 614 as well as being created in the package with the UV energy from the first set of UV sources 630, 632, more quickly creates a desired concentration of ozone in the package that can be also monitored and regulated more effectively by one or more sensors in the package 608. For example, a sensor can be located in the nozzle 614 to monitor ozone gas concentration in the package 608. Gas can puffed into the package head space 617,619, by the pump 616 drawing the gas through the gas coupling pipe 613 from the ambient atmosphere in the container 602. Alternatively, the pump 616 can draw out the gas from the head space 617, 619 in the package 608 and route this gas back out to the ambient atmosphere in the container 602. This puffing movement of gas using the pump 616 to direct gas into and out of the package 608 will provide a quicker process for creating a desired concentration of ozone atmosphere in the head space 617, 619, in the package 608. This ozone in the package 608 will contact and treat the surfaces of the product 606 at a desired concentration which will provide the sanitizing, disinfecting, and sterilizing treatment to the product 606 in the package 608. Additionally, the UV energy from the first set of UV sources 630, 632 creates additional ozone in the package 608 that helps increase the ozone concentration in the package more quickly. The pump 616 can also draw the gas from the atmosphere in the package 608 thereby vacuuming out this gas through the nozzle labeled A 614 and directing that gas into the chamber 602 via the gas coupling pipe 613. To aide in the movement of the gas within the package 608, optionally, a support grid 625 to raise and separate the surfaces of the product 606 from the direct contact with the inner surface of the package material 608 thereby allowing for some path to move gas there between.

This alternating puffing and drawing of gas into and out of the package 608 is a controllable process with the sensors in the package monitoring the desired concentration of ozone at all times.

A second set of UV sources 634, 636, provide UV energy into the operating environment in the container 602. This UV energy is at a UV frequency range that tends to convert ozone back to oxygen. It additionally provides UV treatment that can accelerate the sanitizing, disinfecting, and sterilizing treatment to the surfaces of the product 606 in the package 608.

The energy from the second set of UV sources 634, 636, can accelerate conversion of ozone in the ambient atmosphere in the container 602 to oxygen to restore an air atmosphere in the environment in the container 602. Additionally, the second set of UV sources 632, 634, transmit UV energy into the package 608 and treat the surfaces of the product 606 exposed to the UV energy. In this way, the combination of the second set of UV sources 634, 636, will convert the ozone gas back to oxygen as well as provide treatment to the surfaces of the product 606 in the package 608. Fans 660, 662, 664, 666, in the chamber 602 can move the gas in the chamber atmosphere to help accelerate the conversion of either oxygen to ozone, or alternatively ozone back to oxygen in the ambient atmosphere in the chamber 602. This movement of the gas in the ambient atmosphere in the chamber 602 helps maintain a more homogeneous concentration of ozone gas throughout the operating environment in the chamber 602. It also helps to accelerate the conversion process because the ozone gas is normally heavier than air and it desirable to expose the ozone gas to the second set of UV sources 633, 634, 636, to help accelerate the conversion process back to oxygen. These gas moving devices, such as fans 660, 662, 664, 666, help the system 600 to more quickly and effectively either create ozone gas from the oxygen in the air in the chamber 602, or create oxygen from the ozone in the ambient atmosphere in the chamber 602. In both modes, whether creating ozone from oxygen or creating oxygen from ozone, the particular set of UV sources being activated 630, 632, 634, 636, will continuously transmit UV energy into the bag 608 and treat the surfaces of the product 606. This accelerates the treatment process of the product 606 in the package 608.

As an alternative mode of creating or removing ozone a second compartment 640 will be discussed in more detail below.

This separate compartment 640 is gas coupled to the inside of the container 602 by gas channels 648, 652 that are controllable by gas valves 646, 650 to quickly allow gas to move or be stopped from moving under control of these valves 650, 646. Gas moving devices, such as fans 642, 643 can be activated by the controller to aid in the movement of gas 644, from the separate compartment 640 to the operating environment in the main container 602 as shown. A separate set of UV sources 638 can be energized to cause the moving gas 634 to convert either from ozone to oxygen or alternatively from oxygen to ozone as desired in a particular instance of an application. Optionally, the pump 616 can be connected through a valve control 653 to either the separate compartment 640 or to the inside of the chamber 602 via the gas coupling path 652.

When a desired concentration of ozone treatment to the surfaces of the product 606 in the package 608 has been attained, and in combination of a desired amount of treatment of UV energy from the UV sources 630, 632, 634, 636, to the surfaces of the product 606 in the package 608 a controllable predictable process for sanitizing, disinfecting, and sterilizing treatment to a product 606 in a package 608 is provided.

When the product 606 in the package 608 has been treated, optionally, the pump 626 can vacuum all the gas from the head space 617, 619, in package 608 and vacuum seal the product in the package. Alternatively, the pump 616 can draw out the gas from the package 608 and then fill the head space 617, 619 with a modified atmosphere gas from the modified atmosphere source 654. For example, in certain applications, a modified atmosphere of one or more of nitrogen, carbon dioxide, and other gases may be desired to be remaining in the package 608 with the treated product 606. After completing treating the product with the combination treatment of UV energy and ozone at a desired concentration, the mouth of the package 610 can be heat sealed at the end of the holder 620 by activating heat sources such as wires 621, 622. This can be done very quickly, such as by a user pressing on the end of the holder 620.

NON-LIMITING EXAMPLES

Although specific embodiments of the subject matter have been disclosed, those having ordinary skill in the art will understand that changes can be made to the specific embodiments without departing from the spirit and scope of the disclosed subject matter. The scope of the disclosure is not to be restricted, therefore, to the specific embodiments, and it is intended that the appended claims cover any and all such applications, modifications, and embodiments within the scope of the present disclosure.

What is claimed is:

1. A method for providing a sanitizing treatment for a product or object while inside a package, the method comprising:
securing, in a gas-tight seal, a gas channel to a mouth of an opening of a package containing a product or object;
providing an atmosphere inside a contained environment containing at least the product or object packaged inside a package;
transmitting ultraviolet energy through the atmosphere inside the contained environment and toward the packaged product or object contained therein;
providing at least one of a sanitizing, disinfecting and sterilizing treatment to the packaged product or object with
UV treatment of the product or object in the package from the ultraviolet energy; and
converting oxygen in the atmosphere inside the contained environment to ozone in the atmosphere and transferring gas containing ozone from the atmosphere inside the contained environment into the package containing the product or object.

2. The method of claim 1, further comprising:
transferring gas containing ozone through the gas channel and into the package containing the product or object; and
providing the at least one of a sanitizing, disinfecting and sterilizing treatment to the packaged product or object with the gas containing ozone transferred into the package.

3. The method of claim 2, wherein the transferring comprises puffing the gas containing ozone into the package.

4. The method of claim 2, wherein the transferring comprises transferring the gas containing ozone into the package from the atmosphere inside the contained environment.

5. The method of claim 2, further comprising:
drawing out gas from inside the package containing the packaged product or object.

6. The method of claim 5, further comprising:
transferring a modified atmosphere gas through the gas channel and into the package containing the product or object.

7. The method of claim 6, wherein the modified atmosphere gas comprising one or more of nitrogen, carbon dioxide, a noble gas, an inert gas, argon gas, and helium.

8. The method of claim 1, further comprising:
providing at least one of a sanitizing, disinfecting and sterilizing treatment to the packaged product or object with at least converting oxygen in the atmosphere between an inside surface of the package of the packaged product or object and the surface of the product or object to ozone in the atmosphere therebetween.

9. A method for providing a sanitizing treatment for a product or object while inside a package, the method comprising:
providing inside a contained environment a product or object that is packaged inside a package;
providing a gas channel in an opening of the package containing the product or object;
providing an atmosphere inside the contained environment containing at least the product or object packaged inside the package;
transmitting ultraviolet energy through the atmosphere inside the contained environment containing at least the product or object packaged inside the package; and
providing at least one of a sanitizing, disinfecting and sterilizing treatment to the packaged product or object with at least converting oxygen in the atmosphere inside the contained environment to ozone in the atmosphere and transferring gas containing ozone from the atmosphere inside the contained environment into the package containing the product or object.

10. The method of claim 9, further comprising:
providing at least one of a sanitizing, disinfecting and sterilizing treatment to the packaged product or object with at least UV treatment of the product or object in the package from the ultraviolet energy.

11. The method of claim 9, comprising:
securing, in a gas-tight seal, the gas channel to a mouth of an opening of the package containing a product or object.

12. The method of claim 9, comprising:
wherein the transferring comprises puffing the gas containing ozone into the package.

13. The method of claim 9, wherein the transferring comprises transferring the gas containing ozone through the gas channel and into the package containing the product or object.

14. The method of claim 9, wherein the package comprises one or more layers of polymer and/or plastic material that is substantially transparent to the ultraviolet energy at ultraviolet energy wavelength range to provide at least one of a sanitizing, disinfecting and sterilizing treatment to the packaged product or object in the package; and the method further comprising:
providing at least one of a sanitizing, disinfecting and sterilizing treatment to the packaged product or object with at least UV treatment of the product or object in the package from the ultraviolet energy.

15. The method of claim 9, wherein the package comprises at least one of rigid, semi-rigid, and flexible, packaging material.

16. The method of claim 9, further comprising
providing at least one of a sanitizing, disinfecting and sterilizing treatment to the packaged product or object with at least converting oxygen in the atmosphere between an inside surface of the package of the packaged product or object and the surface of the product or object to ozone in the atmosphere therebetween.

17. The method of claim 9, wherein the transferring comprises transferring, with assistance from a pump, the gas containing ozone through the gas channel and into the package containing the product or object.

18. The method of claim 9, further comprising:
providing at least one of a sanitizing, disinfecting and sterilizing treatment to the packaged product or object with at least transferring gas containing ozone from a separate source, other than from the atmosphere inside the contained environment, through the gas channel and into the package containing the product or object.

19. The method of claim 9, further comprising:
drawing out gas from inside the package containing the packaged product or object.

20. The method of claim 19, further comprising:
transferring a modified atmosphere gas through the gas channel and into the package containing the product or object, wherein the modified atmosphere gas comprising one or more of nitrogen, carbon dioxide, a noble gas, an inert gas, argon gas, and helium.

* * * * *